US009901601B2

(12) United States Patent
Kishida et al.

(10) Patent No.: US 9,901,601 B2
(45) Date of Patent: Feb. 27, 2018

(54) METHOD FOR PREPARING DECELLULARIZED TISSUE PRODUCT, AND GRAFT PROVIDED WITH DECELLULARIZED TISSUE PRODUCT

(75) Inventors: Akio Kishida, Tokyo (JP); Seiichi Funamoto, Hokkaido (JP); Yoshihide Hashimoto, Saitama (JP); Jun Negishi, Chiba (JP); Souichiro Kuwa, Tokyo (JP); Takao Ema, Nagano (JP); Kuniharu Kobayashi, Nagano (JP)

(73) Assignee: ADEKA CORPORATION, Tokyo (JP)

( * ) Notice: Subject to any disclaimer, the term of this patent is extended or adjusted under 35 U.S.C. 154(b) by 958 days.

(21) Appl. No.: 14/342,293

(22) PCT Filed: Sep. 3, 2012

(86) PCT No.: PCT/JP2012/072374
§ 371 (c)(1),
(2), (4) Date: Jun. 16, 2014

(87) PCT Pub. No.: WO2013/032009
PCT Pub. Date: Mar. 7, 2013

(65) Prior Publication Data
US 2015/0157667 A1  Jun. 11, 2015

(30) Foreign Application Priority Data
Sep. 2, 2011 (JP) .................................. 2011-191610

(51) Int. Cl.
*A61K 35/12* (2015.01)
*C12N 5/00* (2006.01)
*C12N 5/02* (2006.01)
*A61K 35/36* (2015.01)
*A61L 27/36* (2006.01)
*A61K 35/30* (2015.01)
*A61K 35/34* (2015.01)

(52) U.S. Cl.
CPC .............. *A61K 35/36* (2013.01); *A61K 35/30* (2013.01); *A61K 35/34* (2013.01); *A61L 27/362* (2013.01); *A61L 27/3604* (2013.01); *A61L 27/3625* (2013.01); *A61L 27/3691* (2013.01); *A61L 2430/40* (2013.01)

(58) Field of Classification Search
None
See application file for complete search history.

(56) References Cited

U.S. PATENT DOCUMENTS

| 6,162,258 A | 12/2000 | Scarborough et al. |
| 2005/0074433 A1 | 4/2005 | Stoll |
| 2006/0253192 A1 | 11/2006 | Atala et al. |
| 2007/0116679 A1 | 5/2007 | Atala |
| 2007/0244568 A1* | 10/2007 | Matsuda .............. A61L 27/3604 623/23.72 |
| 2010/0145444 A1 | 6/2010 | Kishida et al. |
| 2011/0044847 A1* | 2/2011 | Kibalo .................. A61K 35/36 422/22 |

FOREIGN PATENT DOCUMENTS

| EP | 1625832 A1 | 2/2006 |
| EP | 2393914 A1 | 12/2011 |
| JP | 07008547 A | 1/1995 |
| JP | 2004505747 A | 2/2004 |
| JP | 2004267482 A | 9/2004 |
| JP | 2008532653 A | 8/2008 |
| JP | 2010063910 A | 3/2010 |
| WO | 2008111530 A1 | 9/2008 |
| WO | 2010044777 A1 | 4/2010 |
| WO | 2010091188 A1 | 8/2010 |

OTHER PUBLICATIONS

Huang Gui-lin, Li Long-jiang, Luo Jing-cong, Li Xue-ying, Song Qi, Song Qing-gao, Preliminary Study on the Preparation and Histocompatibility of Acellular Tracheae Matrix, Journal of Oral and Maxillofacial Surgery, Dec. 31, 2006, vol. 16 No. 4 pp. 296-299, with English abstract.
Office Action for Chinese Patent Application No. 201280042750.4; dated Aug. 19, 2016.
Yin Meng, Liu Jin-fen, Toshia Fujisato, Kenji Minatoya, Takeshi Nakatani, Tissue-engineered blood vessel scaffolds with valves prepared by hyperpressure acellular technique, Journal of Clinical Rehabilitative Tissue Engineering Research, May 6, 2008, vol. 12, No. 19, pp. 3605-3608, with English abstract.
Akio Kishida et al., "Development of Raw Materials for Regenerative Medicine by High Pressure Treatment", Tokyo Medical and Dental University, Institute of Biomaterials and Bioengineering, 2008, No. 33, pp. 26-31.
Funamoto, S., et al., The use of high-hydrostatic pressure treatment to decullularize blood vessels, Biomaterials, 2010, vol. 31, No. 13, pp. 3590-3595.
Peter S. McFetridge et al: "Endothelial and Smooth Muscle Cell Seeding onto Processed Ex Vivo Arterial Scaffolds Using 3D Vascular Bioreactors", ASAIO Journal, vol. 50, No. 6, Nov. 1, 2004 (Nov. 1, 2004), pp. 591-600, XP055181112.
The Extended European Search Report issued to EP Application No. 12827099.8; dated Apr. 16, 2015.

* cited by examiner

*Primary Examiner* — Christopher R Tate
*Assistant Examiner* — Douglas F White
(74) *Attorney, Agent, or Firm* — Cantor Colburn LLP

(57) ABSTRACT

Provided are: a method for preparing a decellularized tissue product in which decellularized tissue can be filled with liquid while changes in the structure of support tissue constituting the decellularized tissue are inhibited; and a graft provided with a decellularized tissue product. The method for preparing a decellularized tissue product includes a reduced-pressure step for bringing an animal-derived decellularized tissue material and a liquid into contact under reduced-pressure conditions, and/or a pressurized step for bringing same into contact under pressurized conditions. The graft is provided with a decellularized tissue product prepared by the method of preparation.

5 Claims, 10 Drawing Sheets

FIG. 2A
IMMERSION
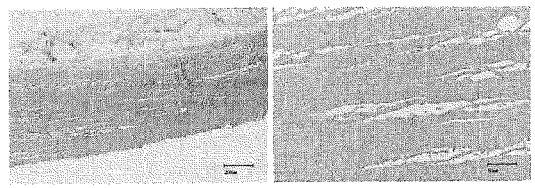
IMPREGNATION
(REDUCED PRESSURE)
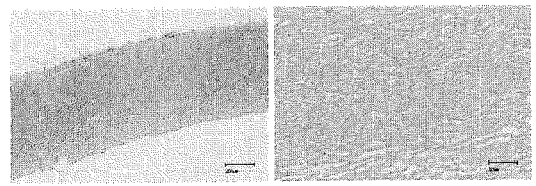
IMPREGNATION
(PRESSURIZATION)
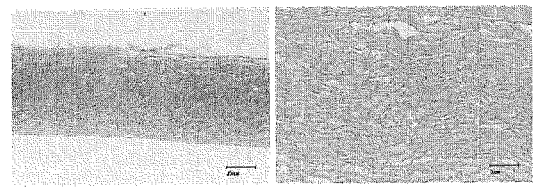
IMPREGNATION
(REDUCED PRESSURE
+ PRESSURIZATION)
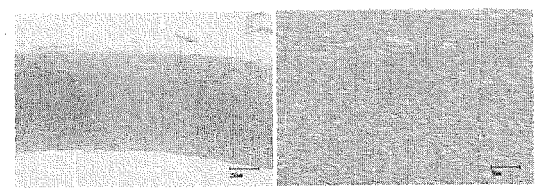
FIG. 2B
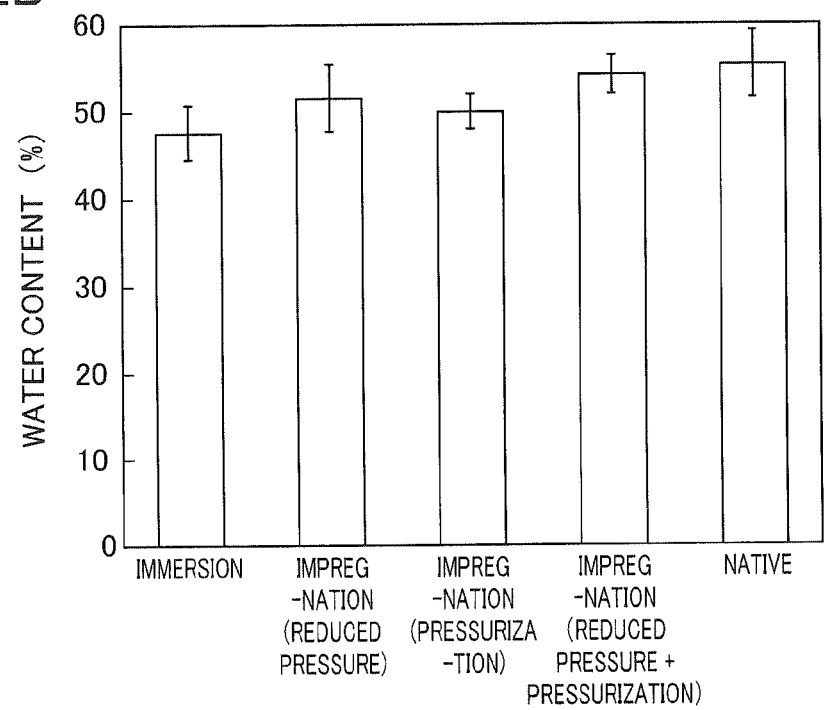

IMMERSION

IMPREGNATION
(−0.01MPa)

IMPREGNATION
(−0.05MPa)

IMPREGNATION
(−0.09MPa)

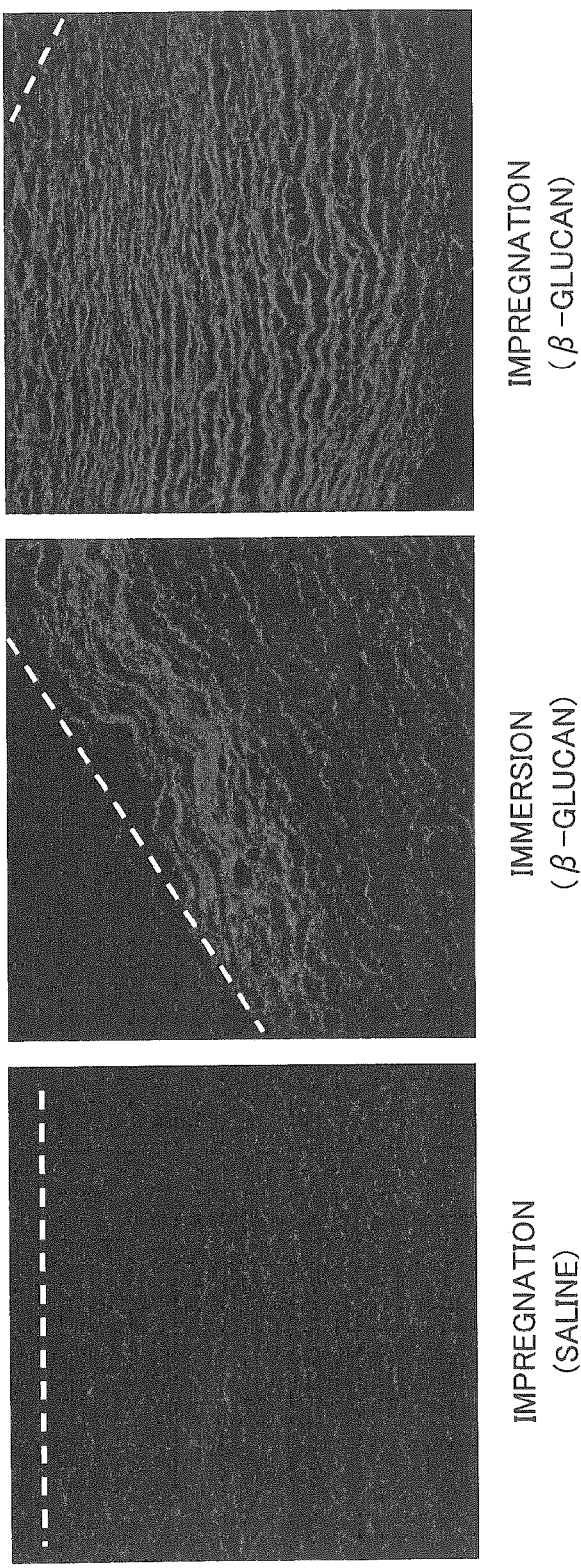

FIG. 8
IMMERSION
(RHODAMINE)
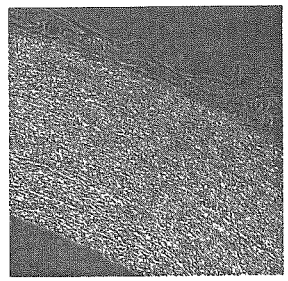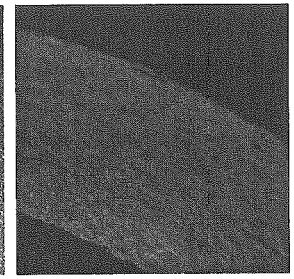
IMMERSION
(RHODAMINE
LABELED PEG)
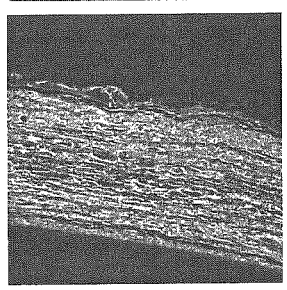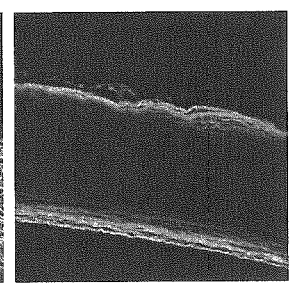
IMPREGNATION
(RAPIDLY DRIED)
(RHODAMINE
LABELED PEG)
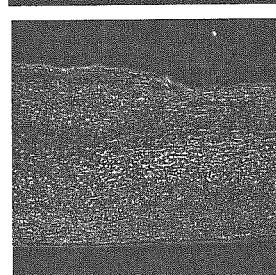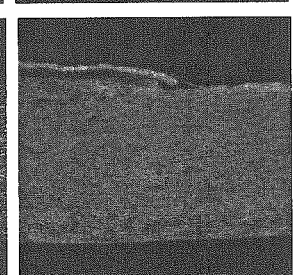
IMPREGNATION
(GRADUALLY DRIED)
(RHODAMINE
LABELED PEG)
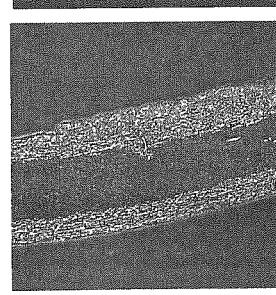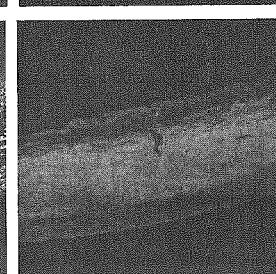

METHOD FOR PREPARING DECELLULARIZED TISSUE PRODUCT, AND GRAFT PROVIDED WITH DECELLULARIZED TISSUE PRODUCT

This is the U.S. national stage of application No. PCT/JP2012/072374, filed on 3 Sep. 2012. Priority under 35 U.S.C. § 119(a) and 35 U.S.C. § 365(b) is claimed from Japanese Application No. 2011-191610, filed 2 Sep. 2011, the disclosure of which is also incorporated herein by reference.

TECHNICAL FIELD

The present invention relates to a method for preparing a decellularized tissue product and a graft provided with a decellularized tissue product.

BACKGROUND ART

In recent years, man-made materials excellent in compatibility with biological tissues have been developed in fields of transplantation therapy and the like. Examples of such man-made materials include technology of using a decellularized tissue, which is a support tissue left after removing cells from a biological tissue, as a graft (e.g., Patent Document 1).

The support tissue (collagen and the like) constituting the biological tissue has voids of various sizes inside it. Typically, these voids are filled with biological substances, water and the like. In recent years, it has been attempted that by filling these voids with functional substances such as proteins, polysaccharides, enzymes and synthesized polymers, functionality is given to the biological tissue, which is then utilized as a biological tissue material.

A method of immersing a biological tissue in a liquid containing a functional substance or the like has been known as such an attempt. However, with a method of the immersion, the functional substance is fixed only in a surface layer of the biological tissue, and it is difficult to fill throughout an inside of the biological tissue with a liquid.

Although it is conceivable to fill the biological tissue with the liquid by heat, microwave, ultrasound or the like, these methods may denature and destroy the support tissue that constitutes the biological tissue, and thus a resulting material can be difficult to be used as a biological tissue material.

Thus, it has been desired to develop a method of being capable of filling the biological tissue with a liquid while changes in a structure of the support tissue constituting the biological tissue are inhibited.

[Patent Document 1] Pamphlet of PCT International Publication No. WO2008/111530

DISCLOSURE OF THE INVENTION

Problems to be Solved by the Invention

It is an object of the present invention to provide a method for preparing a decellularized tissue product in which a biological tissue can be filled with a liquid while changes in a structure of a support tissue constituting the biological tissue are inhibited, and a graft provided with the decellularized tissue product.

Means for Solving the Problems

The present inventors have found that a tissue can be filled with a liquid while changes of a structure of collagen and the like constituting a biological tissue are inhibited by a reduced pressure step of bringing an animal-derived decellularized tissue material and a liquid into contact under a reduced pressure condition and/or a pressurized step of bringing the same into contact under a pressurized condition, and have completed the present invention. The present invention specifically provides the followings.

(1) A method for preparing a decellularized tissue product, comprising a reduced pressure step of bringing an animal-derived decellularized tissue material and a liquid into contact under a reduced pressure condition and/or a pressurized step of bringing the same into contact under a pressurized condition.

(2) The method according to (1), wherein the reduced pressure step is performed at a vacuum degree of 0 to −0.101 MPa.

The method according to (1) or (2), further comprising the pressurized step subsequent to the reduced pressure step.

(4) The method according to any one of (1) to (3), wherein the decellularized tissue material is a lyophilized decellularized tissue.

(5) The method according to (4), wherein the decellularized tissue material is a decellularized tissue lyophilized after being immersed in a treatment solution.

(6) The method according to any one of (1) to (5), wherein the liquid comprises a functionality imparting agent.

(7) A graft to be transplanted in an animal and provided with a decellularized tissue product prepared by the method according to any one of (1) to (6).

Effects of the Invention

According to the present invention, the tissue can be filled with the liquid while the changes in the structure of the support tissue constituting the biological tissue are inhibited, by the reduced pressure step of bringing the animal-derived decellularized tissue material and the liquid into contact under the reduced pressure condition and/or the pressurized step of bringing the same into contact under the pressurized condition.

BRIEF DESCRIPTION OF THE DRAWINGS

FIG. 2A is a view showing cross-sections of aorta after being restored by immersion or impregnation of lyophilized decellularized aorta.

FIG. 2B is a graph showing water contents in aorta after being restored by immersion or impregnation of lyophilized decellularized aorta.

FIG. 6 is a view showing cross-sections of cornea after lyophilized decellularized cornea was immersed in or impregnated with a β-glucan solution.

(A) shows a result of staining with hematoxylin and eosin.

(B) shows a result of staining with Masson trichrome.

FIG. 8 is a view showing cross-sections of aorta after decellularized aorta lyophilized under various freezing conditions was immersed in or impregnated with a rhodamine solution or a rhodamine labeled PEG solution.

Figure 9:
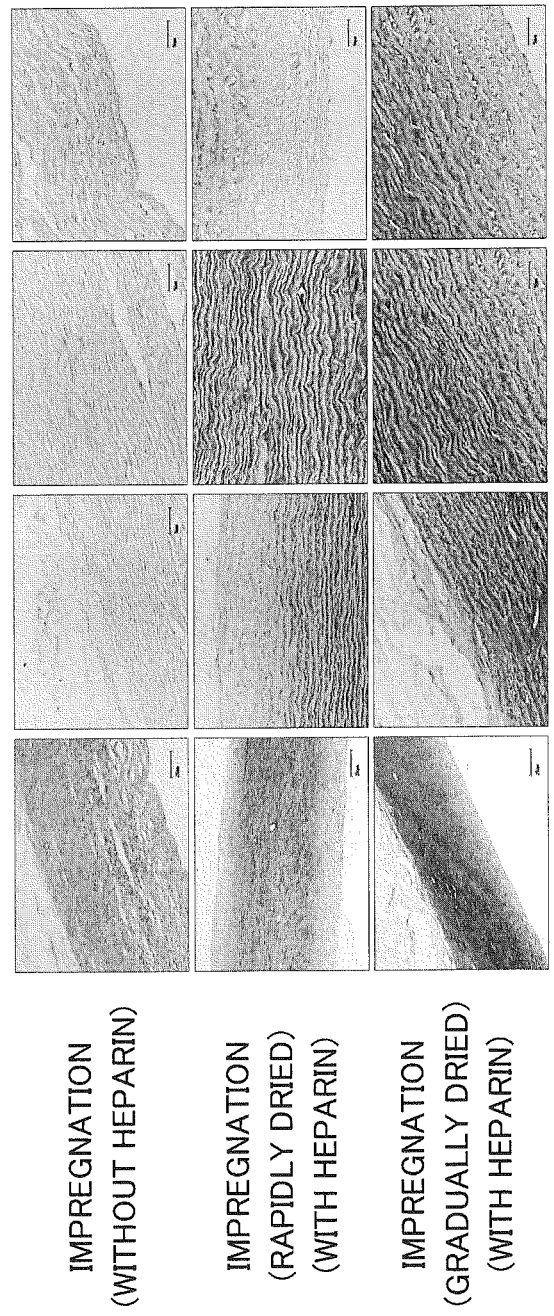

FIG. 9 is a view showing cross-sections of aorta after decellularized aorta lyophilized under various freezing conditions was impregnated with a heparin solution.

Figure 10:
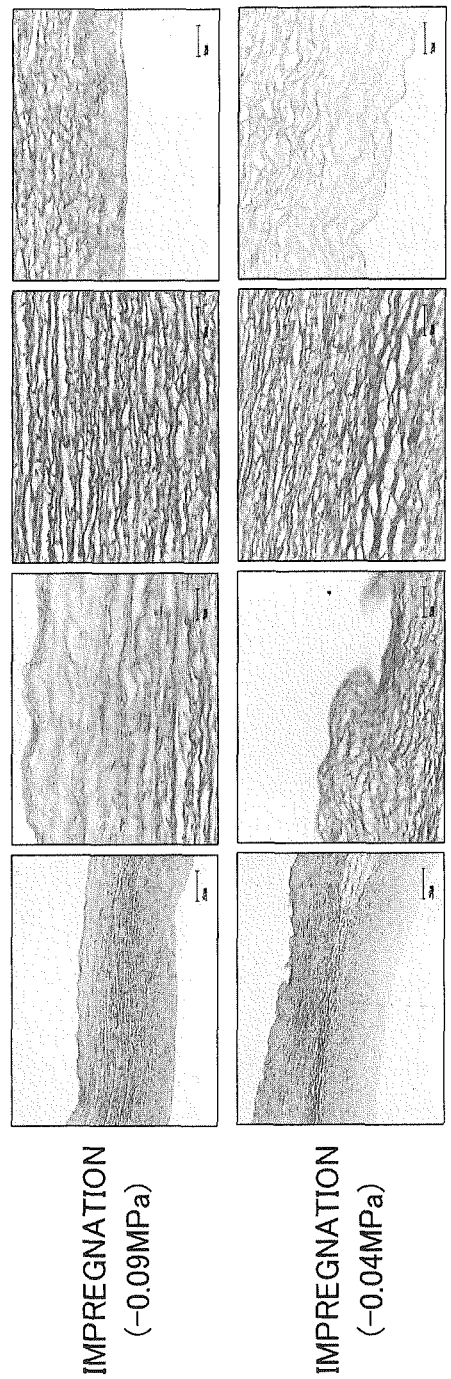

FIG. 10 is a view showing cross-sections of cornea after decellularized cornea lyophilized under various freezing conditions was restored by impregnation.

PREFERRED MODE FOR CARRYING OUT THE INVENTION

Hereinafter, embodiments of the present invention will be described, but they are not intended to limit the present invention.

Reduced Pressure Step and/or Pressurized Step

The preparation method of the present invention comprises a reduced pressure step of bringing an animal-derived decellularized tissue material and a liquid into contact under a reduced pressure condition and/or a pressurized step of bringing the same into contact under a pressurized condition. Hereinafter, a condition in which a decellularized tissue material has been filled with a liquid under the reduced pressure condition or the pressurized condition of the present invention is referred to as "impregnation".

(Reduced Pressure Step)

Many voids are present in a support tissue (collagen and the like) constituting a decellularized tissue material. Water, biological materials, gas and the like are present inside this void. In the preparation method of the present invention, difference in osmotic pressure can occur between an inside and an outside of the decellularized tissue material when water and the like inside the void in the support tissue constituting the decellularized tissue material is brought into contact with an introduced liquid. In such a case, the water and the like inside the void in the support tissue constituting the decellularized tissue material can be replaced physically with the introduced liquid under the reduced pressure condition. Once the introduced liquid enters inside the void in the support tissue, the impregnation of the decellularized tissue material with the liquid is accelerated. Also in the preparation method of the present invention, the gas and the like inside the void in the support tissue constituting the decellularized tissue material can be replaced physically with the introduced liquid under the reduced pressure condition. When air in the decellularized tissue material is discharged and reduced from the tissue under the reduced pressure condition, the void in the decellularized tissue material becomes a reduced pressure state equivalent to that in the decellularized tissue material surrounding it. Then, the introduced liquid is estimated to permeate into the void in the decellularized tissue material.

By either or both of above actions, the decellularized tissue material is preferably impregnated with the liquid. Also according to the preparation method of the present invention, by the above actions, it is possible to evenly impregnate the decellularized tissue material with the liquid while the changes in the structure of the support tissue constituting the decellularized tissue material are inhibited. Also, the decellularized tissue material is preferably impregnated with the liquid having a low compatibility with decellularized tissue material. The above actions can be promoted by further performing the pressurized step described later.

In the reduced pressure step, the pressure may be reduced at least once in a process of impregnating the decellularized tissue material with the liquid. For example, the decellularized tissue material may be brought into contact with the liquid by injecting the liquid while the pressure of an atmosphere of the decellularized tissue material is reduced and a reduced pressure state is kept, or the pressure may be reduced after bringing the decellularized tissue material into contact with the liquid by the immersion or the like.

The reduced pressure condition may be the pressure lower than an atmospheric pressure, and a vacuum degree may be kept at 0 to −0.101 MPa. The "vacuum degree" in the present invention is represented as a gauge pressure. This value indicates to what extent the pressure comes close to an ideal vacuum state (absolute vacuum) when the atmospheric pressure is made zero. The ideal vacuum state in the present invention is the vacuum degree of −0.101 MPa, and the closer to this value, the pressure comes closer to the ideal vacuum state. Also, "keeping" of the pressure in the present invention does not require keeping the pressure in the above range throughout the reduced pressure step, and the pressure may be reduced in this pressure range for at least a certain period (e.g., 0.01 second to 24 hours) for the decellularized tissue material. When the pressure is reduced in this pressure range, the decellularized tissue material becomes evenly impregnated with the liquid.

Also, the pressure range can be adjusted appropriately depending on the liquid to be used upon impregnation. For example, when the decellularized tissue material contains water and the like, if the water and the like are brought into contact with the introduced liquid, the difference in osmotic pressure can occur between the inside and the outside of the decellularized tissue material. At that time, when the pressure close to the absolute vacuum is employed, water, the liquid and the like may vaporize before physically replacing the water and the like with the introduced liquid due to the difference in osmotic pressure. The vaporized water and the like can freeze on a surface of the decellularized tissue material, destroy a surface structure of the decellularized tissue material, and prevent the decellularized tissue material from being impregnated with the liquid. Therefore, in such a case, it is preferable that the pressure be brought close to the atmospheric pressure or an additive be added for the purpose of cooling the liquid or adjusting a vapor pressure.

Also when the decellularized tissue material is a dry, in the case of impregnating this decellularized tissue material with the liquid containing a polymer and the like, if the pressure close to the absolute pressure is employed, the liquid is rapidly indrawn into the decellularized tissue material, while polymers and the like deposit on the surface of the decellularized tissue material. As a result, the support tissue of the decellularized tissue material is deformed and the impregnation of the decellularized tissue material with the liquid may be prevented. In such a case, in order to evenly impregnate the decellularized tissue material with the liquid, it is preferable that the pressure close to the atmospheric pressure be employed or the pressure be reduced to a high vacuum state stepwise after bringing the decellularized tissue material into contact with the liquid.

A time period for the reduced pressure is not particularly limited, and may be one second to 60 minutes and preferably 5 seconds to 10 minutes. According to the present invention, due to the impregnation under the reduced pressure, the inside of the decellularized tissue material is impregnated with the liquid even if a time period for the contact of the decellularized tissue material with the liquid is short, compared with methods such as the immersion performed under the atmospheric pressure.

After bringing the decellularized tissue material into contact with the liquid under the reduced pressure, the reduced pressure condition can be released and the pressure can be elevated to approximately the atmospheric pressure (about 0.1 MPa) to collect the decellularized tissue product. At that time, the elevation of the pressure can facilitate the impregnation of the decellularized tissue material with the liquid.

(Pressurized Step)

In the preparation method of the present invention, the introduced liquid is permeated inside the voids in the decellularized tissue material under the pressurized condition. It is inferred that the liquid is pushed inside the voids in the decellularized tissue material by the pressurization and permeated therein. This evenly impregnates the decellularized tissue material with the liquid while the changes in the structure of the support tissue constituting the decellularized tissue material are inhibited. The decellularized tissue material is preferably impregnated with the liquid even if the compatibility between the decellularized tissue material and the liquid is low.

A method in which the pressure is increased at least once in a process of impregnating the decellularized tissue material with liquid may be employed as the pressurized step of bringing the decellularized tissue material and the liquid into contact under the pressurized condition. For example, the decellularized tissue material and the liquid may be brought into contact by injecting the liquid while the atmosphere of the decellularized tissue material is pressurized and the pressurized state is kept, or the pressure may be increased after the decellularized tissue material and the liquid are brought into contact by immersion or the like.

An increased pressure condition may be a pressure higher than the atmospheric pressure. When the atmospheric pressure is made 0 atmosphere, the increased pressure may be kept at 0.1 to 10000 atmospheres, preferably 0.1 to 1000 atmospheres, and particularly preferably 0.1 to 100 atmospheres. Also when the atmospheric pressure is 1000 atmospheres or higher, cells of indigenous bacteria are thoroughly destroyed and survival of the indigenous bacteria in the decellularized tissue material is inhibited. The pressure can be controlled appropriately depending on components included in the liquid and an extent that the decellularized tissue material is impregnated with the liquid or the like. Keeping the pressure referred to here does not require keeping the pressure in this range throughout the pressurized step. The decellularized tissue material may be pressurized in this pressure range at least for a certain period of time (e.g., 0.01 second to 24 hours). Such pressurization can be performed using, for example, an instrument such as a type 1 pressure vessel, a type 2 pressure vessel or a small type pressure vessel defined in Industrial Safety and Health Act depending on values and the like of the pressure to be used for the pressurization.

A time period for the pressurization is not particularly limited, but may be one second to 24 hours and preferably one minute to 60 minutes. According to the present invention, due to the impregnation under the pressurized condition, the inside of the decellularized tissue material is impregnated with the liquid even if a time period for the contact of the decellularized tissue material with the liquid is short, compared with methods such as the immersion performed under the atmospheric pressure.

Temperature for the pressurization is not particularly limited as long as the decellularized tissue material is not denatured, and may be −20 to 30° C. and preferably −10 to 25° C.

In the preparation method of the present invention, the reduced pressure step may be combined with the pressurized step. In the reduced-pressure step and the pressurized step, either one may be performed in first. Performing the pressurized step after the reduced-pressure step is particularly preferable in that the even impregnation throughout the tissue can be realized rapidly because the permeation of the liquid into the decellularized tissue material can be accelerated after decreasing air in the decellularized tissue material.

Decellularized Tissue Material

The decellularized tissue material can be prepared by a conventionally known method (e.g., WO2008/11530, Pamphlet).

The decellularized tissue material may be used directly after its preparation, or a conservation treatment typically performed (lyophilization treatment, freezing treatment, drying treatment and the like) may be given thereto. According to the preparation method of the present invention, the impregnation can be facilitated by physically replacing the water, the gas, and the like inside the voids in the support tissue constituting the decellularized tissue material with the introduced liquid in the aforementioned reduced pressure step, regardless of the presence or absence of the conservation treatment of the decellularized tissue material. The lyophilized decellularized tissue material is preferable in that the impregnation can particularly be facilitated by physically replacing the gas and the like inside the voids in the support tissue constituting the decellularized tissue material with the introduced liquid. Also when the decellularized tissue material is lyophilized, even if the polymer and the like are contained in the liquid to be introduced, the polymer and the like are difficult to deposit on the surface of the decellularized tissue material, and thus, the decellularized tissue material can preferably be impregnated with the liquid. According to the present invention, the decellularized tissue material can be restored while the changes of the structure of the decellularized tissue material to which the conservation treatment has been given are inhibited.

A method for lyophilizing the decellularized tissue material is not particularly limited, and includes a method of drying in vacuum after freezing the decellularized tissue material by immersion in liquid nitrogen, rapid lyophilization by dry ice, gradual lyophilization at −80 to −4° C. using a freezer (manufactured by Nihon Freezer Co., Ltd.), or controlled lyophilization at −10 to −80° C. using a programmed freezer, or the like.

The decellularized tissue material may be lyophilized after being immersed in any solvent typically used for storing the decellularized tissue material, but particularly preferably is lyophilized after being immersed in a treatment solution. The treatment solution includes solutions containing disaccharides such as sucrose, trehalose, lactose, maltose cellobiose and the like, trisaccharides such as raffinose, melezitose, maltotriose and the like, glycerine, ribitol, galactitol, xylitol, sorbitol, erythritol, mannitol, maltitol and the like alone or in combination, or solutions in which these are dissolved in water, buffer, saline, or the like. Components in these treatment solutions can be bound to free water in the decellularized tissue material, and can appropriately remove the water from the decellularized tissue material without increasing the osmotic pressure and causing denaturation and swelling of proteins in the decellularized tissue material. This inhibits the change of the support tissue in the decellularized tissue material. By performing the immersion in such a treatment solution before the lyophilization, it becomes possible to store the decellularized tissue material for a long period of time while the change of the original structure of the decellularized tissue material is inhibited also after the lyophilization.

A condition for immersing in the solvent may be a condition at 4 to 30° C. for 30 minutes to one day.

An animal from which the decellularized tissue material in the present invention is derived is not particularly limited, and can include mammalian animals such as swine, cattle, horses, goats, sheeps, rabbits, kangaroos, monkeys, humans, and the like.

The decellularized tissue in the present invention is not particularly limited, and can include tissues derived from organs such as cornea, cardiac valve, blood vessel, skin, cartilage, bone, tendon, muscle, urinary bladder, small intestine, heart, liver, lung, trachea, esophagus, crystal lens, vitreous body, retina, nerve, fat tissue, brain, dura mater, pleural membranes, diaphragm, urinary duct, kidney, pancreas, gallbladder, gingiva, periodontal membrane, tooth, placenta, reproductive organs, and the like.

Liquid

The liquid that is brought into contact with the decellularized tissue material and impregnates may be a liquid upon contact, and is not particularly limited. Liquids such as a solution, a slurry liquid, a dispersion and the like can be used.

Such a liquid may contain a functionality imparting agent. The functionality imparting agent refers to an agent containing a substance that acts upon a physiological function in the living body. The functionality imparting agent is not particularly limited, and examples thereof include low molecular medicines (aspirin and the like), natural medicinal substance (antibiotics and the like), proteins (growth factors and the like), polymerizable monomers, polysaccharides (heparin, β-glucan and the like), nucleic acids (plasmids and the like), synthesized polymers (polyethylene glycol (PEG) and the like), lipids (cholesterol and the like), surfactants and the like, and combinations thereof. Also the functionality imparting agent may be a liquid, a solid, or a mixture thereof.

When a plurality of reactive substances (polymerizable monomers and the like) is contained as the functionality imparting agent, these reactive substances can also be reacted chemically one another after impregnating the decellularized tissue material.

In the preparation method of the present invention, the decellularized tissue material can preferably be impregnated with the liquid, regardless of physical properties of the liquid. Thus, the decellularized tissue material can preferably be impregnated with, for example, a highly viscous substance (β-glucan and the like), a substance that is poorly compatible with the decellularized tissue material (e.g., hydrophobic substance such as heparin and the like), or a polymer substance (polyethylene glycol and the like).

Decellularized Tissue Product

Whether a decellularized tissue product in which the decellularized tissue material had been impregnated with the liquid is obtained or not can be known by measuring an indicator depending on the introduced liquid for the decellularized tissue product. For example, when the decellularized tissue material is impregnated with an aqueous solution, this can be known by measuring a water content ratio and the like in the decellularized tissue product. Also when the decellularized tissue material was impregnated with a certain substance, this can be known by staining the decellularized tissue product with a reagent that can stain the certain substance.

Graft

The decellularized tissue product obtained from the preparation method of the present invention is useful as a constitution of a graft to be transplanted in an animal. That is, the graft of the present invention is provided with the aforementioned decellularized tissue product.

EXAMPLES

Example 1: Restoration of Lyophilized Decellularized Cornea-I

[Decellularization of Cornea]

Cornea was removed from a swine eyeball, and washed with a PBS solution. A basic medium in which M199 medium and MEMα medium were mixed at 1:1 (hereinafter referred to as "Mα medium") was made, and 10% by mass of glycerol was added thereto. The cornea was placed together with this solution in a bag made from polyethylene film to wet the cornea, and then the bag was sealed with a heat sealer. This bag was placed in a chamber of "Dr. CHEF" (manufactured by Kobe Steel Ltd.), and an ultrahigh hydrostatic pressure at 6000 atmospheres was applied for 10 minutes while temperature was kept at 10° C. A rate for increased pressure/reduced pressure was 1200 atmospheres/minute.

Subsequently, the cornea after applying the pressure was transferred in a sterilized cup (200 mL) under a clean environment, and 50 mL of Ma medium for washing (0.02% by mass of Dnase and 3.5% by mass of dextran were added to the Mα medium) was added thereto. The cornea was washed at 23° C. for 24 hours and then further washed at 23° C. for 24 hours with the exchanged washing solution to remove cells inside the cornea to obtain decellularized cornea.

[Lyophilization of Decellularized Cornea]

The above decellularized cornea was immersed in the treatment solution (using sucrose) at 20° C. for 90 minutes. Then, the decellularized cornea was frozen using liquid nitrogen. The frozen decellularized cornea was dried in a vacuum state using a lyophilizer (manufactured by Tokyo Rikakikai Co., Ltd.) to obtain lyophilized decellularized cornea.

[Restoration of Lyophilized Decellularized Cornea]

(Restoration by Immersion)

The above lyophilized decellularized cornea was immersed in saline at 20° C. for 6 hours.

(Restoration by Impregnation)

The above lyophilized decellularized cornea was placed in a stainless vacuum tube, and a vacuum degree in the stainless vacuum tube was made −0.09 MPa using a vacuum pump. Further, saline was injected in the stainless vacuum tube, and the vacuum degree was kept for 5 minutes. The stainless vacuum tube was released to the atmospheric pressure, and the decellularized cornea was placed together with saline in a polyethylene bag, which was then sealed. A high hydrostatic pressure at 100 atmospheres was applied to the sealed decellularized cornea at 25° C. for 15 minutes using a cold isostatic pressing apparatus (manufactured by Kobe Steel Ltd.).

(Evaluation of Restoration)

Figure 1:
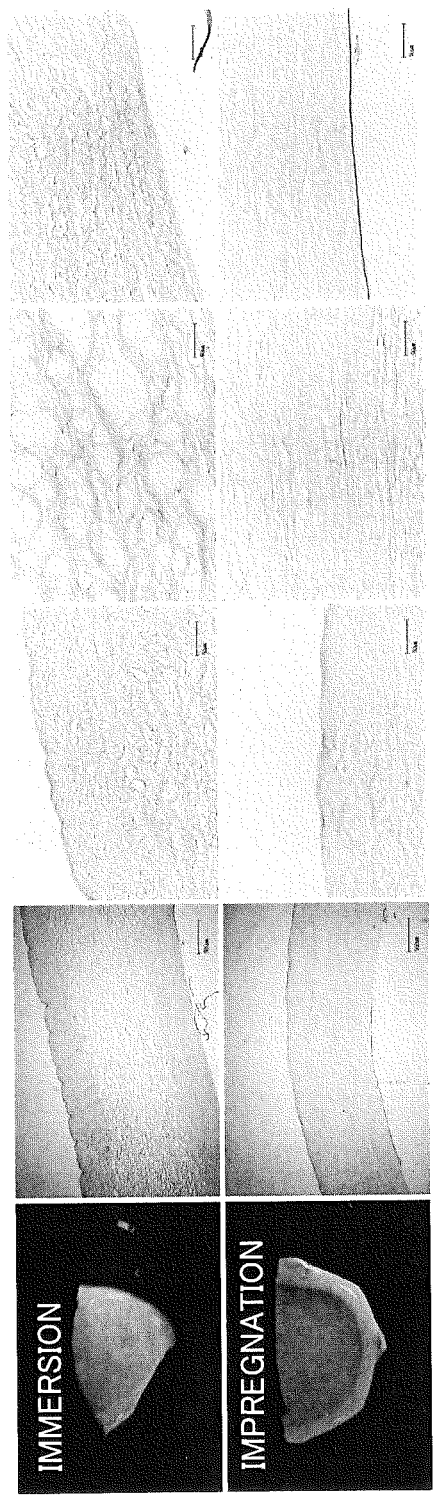
FIG. 1 is a view showing cross-sections of cornea after being restored by immersion or impregnation of lyophilized decellularized cornea.

The decellularized cornea restored by the immersion or the impregnation was stained with eosin. Extracellular matrices such as collagen and the like are stained by staining the cornea with eosin. The results are shown in FIG. 1. A cross-section of the decellularized cornea restored by the immersion was not evenly stained, and thus, saline was not permeated evenly upon restoration. Also, a collagen structure in the cornea was broken. On the other hand, the decellularized cornea restored by the impregnation was evenly stained, and thus saline was permeated evenly upon restoration. Changes in the collagen structure in the cornea were inhibited.

Example 2: Restoration of Lyophilized Decellularized Aorta

The decellularization and the lyophilization were performed to obtain lyophilized decellularized aorta in the same manner as in Example 1, except that swine aorta was used as an animal derived tissue.

[Restoration of Lyophilized Decellularized Aorta]
(Restoration by Immersion)

The above lyophilized decellularized aorta was immersed in saline at room temperature for 6 hours.

(Restoration by Impregnation)

The lyophilized decellularized aorta was impregnated with saline by the following three methods.

(1) Impregnation by Reduced Pressure

The lyophilized decellularized aorta was placed in a stainless vacuum tube, and a vacuum degree in the stainless vacuum tube was made −0.09 MPa using the vacuum pump. Saline was injected in the stainless vacuum tube, and the vacuum degree was kept for 5 minutes.

(2) Impregnation by Pressurization

The lyophilized decellularized aorta was placed together with saline in a polyethylene bag, which was then sealed. A high hydrostatic pressure at 100 atmospheres was applied to the sealed decellularized aorta at 25° C. for 15 minutes using the cold isostatic pressing apparatus (manufactured by Kobe Steel Ltd.).

(3) Impregnation by Reduced Pressure and Pressurization

The lyophilized decellularized aorta was placed in a stainless vacuum tube, and a vacuum degree in the stainless vacuum tube was made −0.09 MPa using the vacuum pump. Then, saline was injected in the stainless vacuum tube, and the vacuum degree was kept for 5 minutes. The stainless vacuum tube was released to the atmospheric pressure, and the decellularized aorta was placed together with saline in a polyethylene bag, which was then sealed. A high hydrostatic pressure at 100 atmospheres was applied to the sealed decellularized aorta at 25° C. for 15 minutes using the cold isostatic pressing apparatus (manufactured by Kobe Steel Ltd.).

(Evaluation of Restoration by Staining with Eosin)

The decellularized aorta restored by the immersion or the impregnation was stained with eosin. The results are shown in FIG. 2(A). The decellularized aorta restored by the immersion was not evenly stained, and thus, saline was not permeated evenly upon restoration. Also, the collagen structure of the aorta was broken. On the other hand, the decellularized aorta restored by the impregnation was evenly stained, and thus saline was permeated evenly upon restoration. The change in the collagen structure of the aorta was inhibited. In particular, the decellularized aorta restored by the impregnation under the reduced pressure and the pressurization was evenly stained, as well as the voids and texture in the collagen structure were completed and the collagen structure was kept extremely well.

(Evaluation of Restoration by Water Content Ratio)

A mass of the decellularized aorta restored by the immersion or the impregnation was measured after removing an excessive liquid with filter paper. This measured value is referred to as a "wet weight". Then, a mass was measured after lyophilizing each decellularized aorta in vacuum. This measured value is referred to as a "dry weight". A water content ratio in each decellularized aorta was calculated based on the following formula.

$$\text{Water content ratio(\% by mass)} = \{(\text{Wet weight} - \text{Dry weight})/\text{Wet weight}\} \times 100$$

The results are shown in FIG. 2(B). The water content ratio in the decellularized aorta restored by the impregnation was equivalent to or higher than the water content ratio in the decellularized aorta restored by the immersion. In particular, the water content ratio in the decellularized aorta restored by the impregnation under the reduced pressure and the pressurization was nearly equal to the water content ratio in native aorta, and thus the decellularized aorta was restored extremely well.

Example 3: Restoration of Lyophilized Decellularized Skin

The decellularization and the lyophilization were performed to obtain lyophilized decellularized skin in the same manner as in Example 1, except that swine skin was used as an animal derived tissue.

[Restoration of Lyophilized Decellularized Skin]
(Restoration by Immersion)

The above lyophilized decellularized skin was immersed in saline at room temperature for 30 minutes.

(Restoration by Impregnation)

The lyophilized skin was placed in a stainless vacuum tube, and a vacuum degree in the stainless vacuum tube was made −0.01 MPa, −0.05 MPa or −0.09 MPa using the vacuum pump. Then, saline was injected in the stainless vacuum tube, and the vacuum degree was kept for 5 minutes. Then, the lyophilized skin was placed together with saline in a polyethylene bag, which was then sealed. A high hydrostatic pressure at 100 atmospheres was applied to the sealed decellularized skin at 25° C. for 15 minutes using the cold isostatic pressing apparatus (manufactured by Kobe Steel Ltd.).

(Evaluation of Restoration by Staining with Eosin)

Figure 3A:
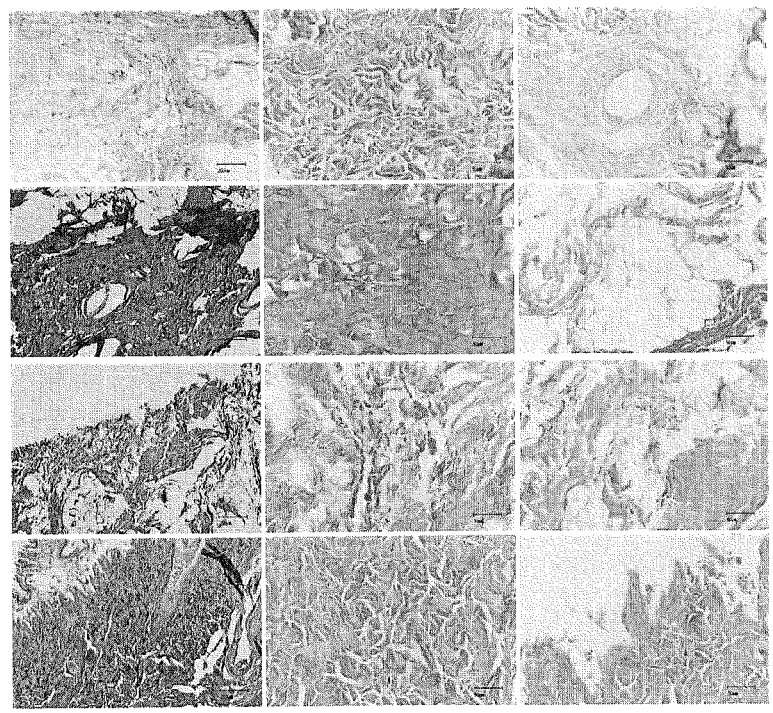
FIG. 3A is a view showing cross-sections of skin after being restored by immersion or impregnation of lyophilized decellularized skin.

The restoration of the decellularized skin was evaluated by staining with eosin in the same manner as in Example 2. The results are shown in FIG. 3(A). The decellularized skin restored by the immersion was scarcely stained, and thus saline was scarcely permeated inside the tissue upon restoration. Also, the collagen structure was broken. On the other hand, collagen was stained in the decellularized skin restored by the impregnation, and thus saline was permeated inside the tissue upon restoration. Also, the change in the collagen structure was inhibited. When the impregnation was performed at a vacuum degree of −0.09 MPa, collagen was evenly stained, as well as the voids and texture in the collagen structure were completed and the collagen structure was kept particularly well.

(Evaluation of Restoration by Water Content Ratio)

Figure 3B:
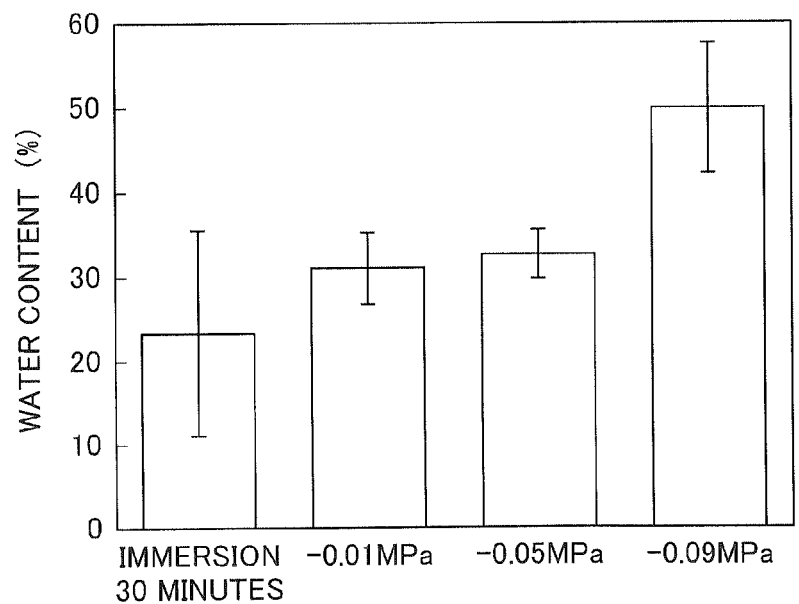
FIG. 3B is a graph showing water contents in skin after being restored by immersion or impregnation of lyophilized decellularized skin.

A water content ratio in each decellularized skin was calculated in the same manner as in Example 2. The results are shown in FIG. 3(B). The water content ratio in the decellularized skin restored by the impregnation was higher than the water content ratio in the decellularized skin restored by the immersion. When the pressure was reduced to the vacuum degree of −0.09 MPa, the water content ratio was particularly high.

Figure 4:
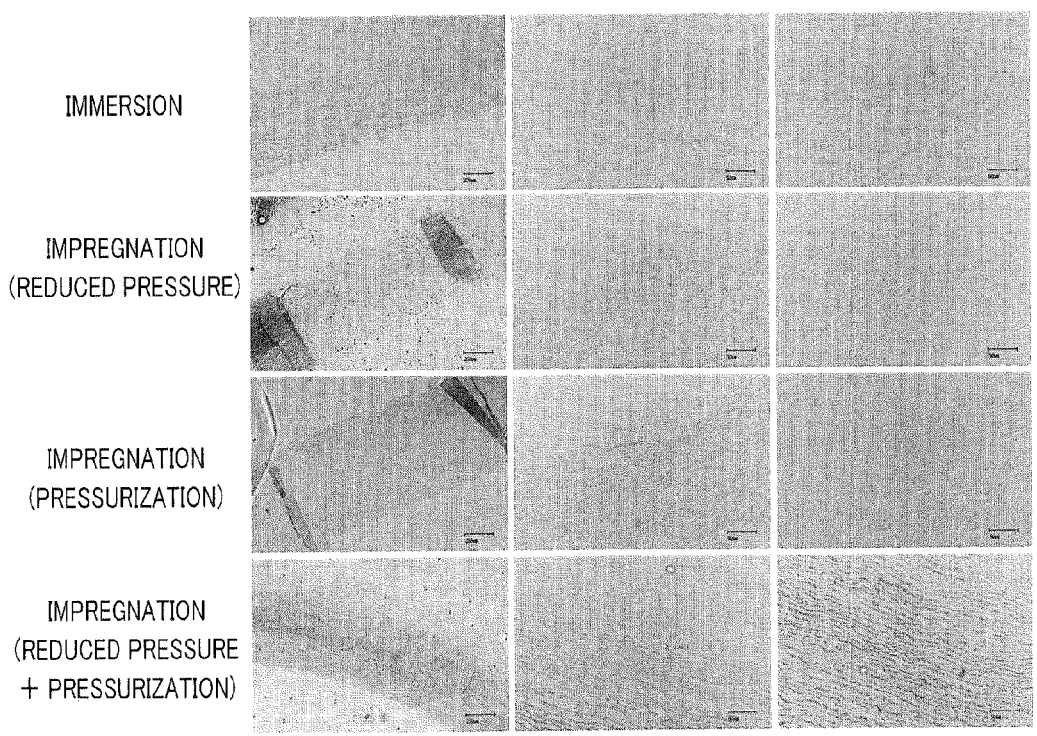
FIG. 4 is a view showing cross-sections of aorta after lyophilized decellularized aorta was immersed in or impregnated with a heparin solution.

Example 4: Functionalization of Lyophilized Decellularized Aorta by Heparin Solution-I Functionalized decellularized aorta was obtained by performing the same treatment as in Example 2, except that saline was replaced with a heparin solution. The resulting decellularized aorta was stained with toluidine blue. A distribution of heparin in the decellularized aorta can be visualized by staining the decellularized aorta with toluidine blue. The results are shown in FIG. 4. Heparin was not permeated in the decellularized aorta functionalized by the immersion. On the other hand, heparin was permeated in the tissue in the decellularized aorta functionalized by the impregnation. In particular, heparin was permeated throughout the tissue in the decellularized aorta functionalized by the impregnation under the reduced pressure and the pressurization.

Figure 5:
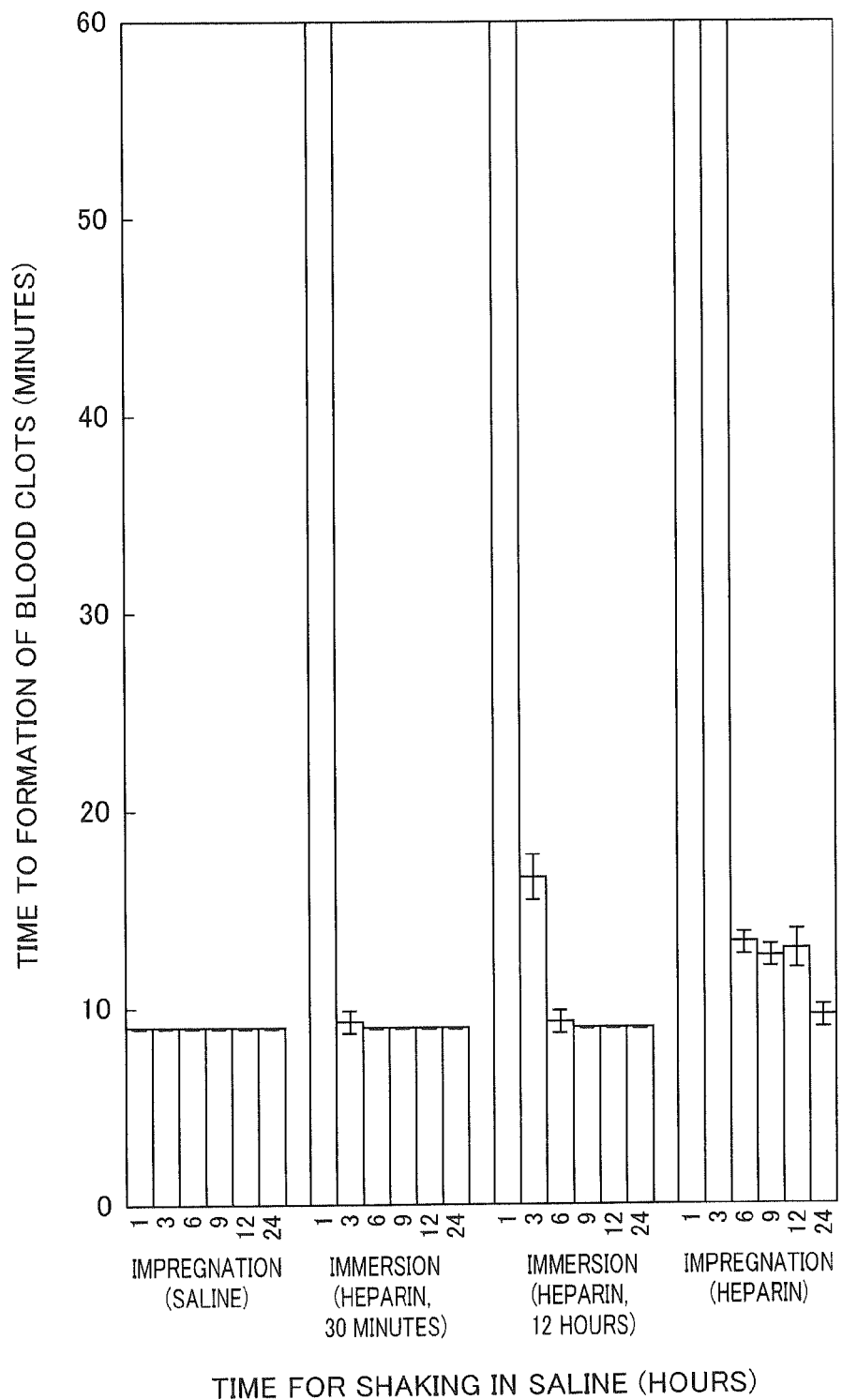
FIG. 5 is a graph showing results of a heparin elution test performed after lyophilized decellularized aorta was immersed in or impregnated with a heparin solution.

Example 5: Functionalization of Lyophilized Decellularized Aorta by Heparin Solution-II Functionalized decellularized aorta was obtained in the same manner as in Example 2, except that saline was replaced with the heparin solution.
[Functionalization of Lyophilized Decellularized Aorta]
(Functionalization by Immersion)
The above lyophilized decellularized aorta was immersed in the heparin solution at room temperature for 30 minutes or 12 hours.
(Functionalization by Impregnation)
The lyophilized decellularized aorta was placed in a stainless vacuum tube, and the vacuum degree in the stainless vacuum tube was made −0.09 MPa using the vacuum pump. Then, the heparin solution or saline was injected into the stainless vacuum tube, and the vacuum degree was kept for 5 minutes. The stainless vacuum tube was released to the atmospheric pressure, and the decellularized aorta was placed together with the heparin solution or saline in a polyethylene bag, which was then sealed. A high hydrostatic pressure at 100 atmospheres was applied to the sealed decellularized aorta at 25° C. for 15 minutes using the cold isostatic pressing apparatus (manufactured by Kobe Steel Ltd.).
(Elution Test of Heparin)
The decellularized aorta functionalized by the immersion or the impregnation was immersed in saline, and shaken at 37° C. Saline was collected at time points of 1, 3, 6, 9, 12 and 24 hours after starting the shaking. Each time when saline was collected, the decellularized aorta was transferred to a new container and saline was newly added to repeat the elution step.
A test by Lee-White method was performed using the collected elution liquid. Specifically, swine whole blood (10 mL) and each collected elution liquid (1 mL) were added to a sterilized polyethylene tube (product name: VIOLAMO manufactured by AS ONE Corporation), and the mixture was incubated at 37° C. A time period from start of the incubation to formation of blood clots was measured for each elution liquid. The results are shown in FIG. 5. The decellularized aorta functionalized by the impregnation exhibited anti-thrombogenicity over a long period of time, indicating that the heparin was kept inside the tissue. Heparin is a high molecular substance and has low compatibility with the decellularized aorta, but according to the present invention, the decellularized aorta can preferably be impregnated with heparin.

Example 6: Functionalization of Lyophilized Decellularized Cornea by β-Glucan Solution Lyophilized decellularized cornea was obtained in the same manner as in Example 1.
[Functionalization of Lyophilized Decellularized Cornea]
(Functionalization by Immersion)
The above lyophilized decellularized cornea was immersed in a 1% β-glucan solution at room temperature for 6 hours.
(Functionalization by Impregnation)
The above lyophilized decellularized cornea was placed in a stainless vacuum tube, and the vacuum degree in the stainless vacuum tube was made −0.09 MPa using the vacuum pump. Then, the 1% β-glucan solution was injected in the stainless vacuum tube, and the vacuum degree was kept for 5 minutes. The stainless vacuum tube was released to the atmospheric pressure, and the decellularized cornea was placed together with the 1% β-glucan solution in a polyethylene bag, which was then sealed. A high hydrostatic pressure at 100 atmospheres was applied to the sealed decellularized cornea at 25° C. for 15 minutes using the cold isostatic pressing apparatus (manufactured by Kobe Steel Ltd.).
(Evaluation of Functionalization by Staining with Calcofluor White)
The decellularized cornea functionalized by the immersion or the impregnation was stained with calcofluor white. The distribution of β-glucan in the decellularized cornea can be visualized by staining with calcofluor white. The results are shown in FIG. 6. A broken line in FIG. 6 denotes a surface of cornea. As shown in FIG. 6, β-glucan was permeated only in a surface portion of the cornea in the decellularized cornea functionalized by the immersion. On the other hand, β-glucan was permeated throughout the tissue in the decellularized cornea functionalized by the impregnation.

Example 7: Xenogeneic Transplant Study of Restored Decellularized Cornea

Figure 7A:
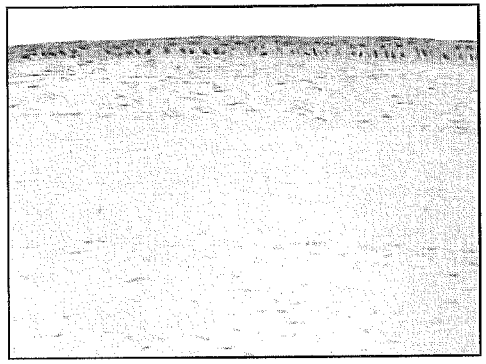
FIG. 7 is a view showing cross-sections of cornea one month after lyophilized decellularized cornea was restored by impregnation and transplanted in a Japanese white rabbit.
Figure 7B:
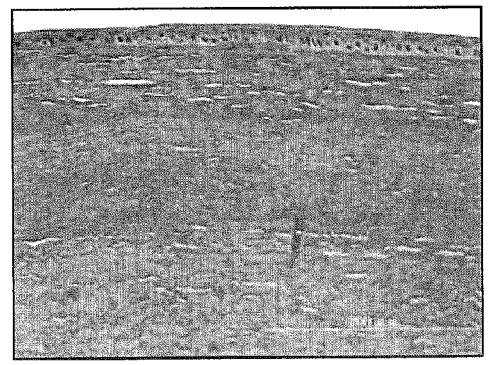

Decellularized cornea derived from the swine and restored by the impregnation was obtained in the same manner as in Example 1. The obtained decellularized cornea was sliced into a thickness of 160 μm using a microkeratome (manufactured by NIDEK Co. Ltd.)
Then, the decellularized cornea was sterilized by a high hydrostatic pressure treatment (10° C., 5000 atmospheres, and for 10 minutes). Just before the transplant, the decellularized cornea was processed into a disc shape having a diameter of 2 mm to use as a graft under a clean environment. Corneal parenchyma in a Japanese white rabbit was cut open, and subsequently delamination was performed to make a pocket for cornea transplant. The graft was inserted into this pocket. The cornea one month after the transplant was stained with hematoxylin/eosin and Masson trichrome. The results are shown in FIGS. 7(A) and 7(B), respectively. Collagen and the like in the graft were stained by staining the cornea with hematoxylin/eosin and Masson chrome, and thus the presence or absence of graft lost and the like after the transplant was found. As shown in FIG. 7, the restored decellularized cornea could be transplanted without causing elimination and rejection after the transplant.

Example 8: Functionalization of Lyophilized Decellularized Aorta by Rhodamine Labeled PEG Solution Lyophilized decellularized aorta was obtained in the same manner as in Example 2.
[Functionalization of Lyophilized Decellularized Aorta]
(Functionalization by Immersion)
The above lyophilized decellularized aorta was immersed in a rhodamine solution or a rhodamine labeled PEG solution at room temperature for 15 minutes.
(Functionalization by Impregnation)
The above lyophilized decellularized aorta was placed in a vacuum pressurization impregnation apparatus (manufactured by F-COM Co., Ltd), and the vacuum degree in this apparatus was made −0.09 MPa. Then, the rhodamine labeled PEG solution was injected in this apparatus, and the vacuum degree was kept for 30 seconds. Then, the pressure in this apparatus was increased, the increased pressure at 3 atmospheres was applied at 25° C. for 15 minutes, and then released to the atmospheric pressure.
(Evaluation of Functionalization by Fluorescence Microscope Using Fluorescent Dye (Rhodamine))
In the decellularized aorta functionalized by the rhodamine solution or the rhodamine labeled PEG solution, the distribution of rhodamine in the decellularized aorta can be visualized by observation under the fluorescence microscope. The results of visualizing the distribution of rhodamine in the decellularized aorta are shown in FIG. 8 (photographs on right side). As shown in FIG. 8 (photographs on right side), although rhodamine was permeated throughout the tissue, rhodamine labeled PEG was permeated only in the surface portion in the decellularized aorta functionalized by the immersion. On the other hand, rhodamine labeled PEG was permeated throughout the tissue in the decellularized aorta functionalized by the impregnation. When the decellularized aorta was gradually dried by a freezer (manufactured by Nihon Freezer Co., Ltd.) when frozen, the inside of the tissue was impregnated with rhodamine labeled PEG at high concentration.

Example 9: Functionalization of Lyophilized Decellularized Aorta by Heparin Solution-III Lyophilized decellularized aorta was obtained in the same manner as in Example 2. In addition, the lyophilized decellularized aorta was obtained by gradually drying the aorta using the freezer (manufactured by Nihon Freezer Co., Ltd.) when the aorta was frozen.
[Functionalization of Lyophilized Decellularized Aorta by Impregnation]
The above lyophilized decellularized aorta was placed in the vacuum pressurization impregnation apparatus (manufactured by F-COM Co., Ltd), and the vacuum degree in this apparatus was made −0.04 MPa. Then, the heparin solution or saline was injected in this apparatus, and the vacuum degree was kept for 30 seconds. Then, the pressure in this apparatus was increased, the increased pressure at 3 atmospheres was applied at 25° C. for 15 minutes, and subsequently released to the atmospheric pressure.
(Evaluation of Functionalization by Staining with Toluidine Blue)
The resulting decellularized aorta was stained with toluidine blue. The results are shown in FIG. 9. Heparin was permeated throughout the tissue in the decellularized aorta functionalized by the impregnation. In particular, the inside of the tissue was impregnated with heparin at high concentration in the decellularized aorta gradually dried when frozen.

Example 10: Restoration of Lyophilized Decellularized Cornea-II

Lyophilized decellularized cornea was obtained in the same manner as in Example 1.
(Restoration of Lyophilized Decellularized Cornea by Impregnation)
The above lyophilized decellularized cornea was placed in the vacuum pressurization impregnation apparatus (manufactured by F-COM Co., Ltd), and the vacuum degree in this apparatus was made −0.09 MPa or −0.04 MPa. Then, saline was injected in this apparatus, and the vacuum degree was kept for 30 seconds. Then, the pressure in this apparatus was increased, the increased pressure at 3 atmospheres was applied at 25° C. for 15 minutes, and subsequently released to the atmospheric pressure.
(Evaluation of Restoration)
The decellularized cornea restored by the impregnation was stained with eosin. The results are shown in FIG. 10. The decellularized cornea restored by the impregnation was evenly stained, and thus the saline was evenly permeated when the cornea was restored. Less intercellular space was observed and the change in the collagen structure of the cornea was inhibited in the tissue impregnated at higher vacuum degree (−0.09 MPa).

The invention claimed is:
1. A method for preparing a decellularized tissue product comprising:
a reduced pressure step comprising bringing an animal-derived decellularized tissue material and a liquid into contact under a reduced pressure condition and
a pressurized step subsequent to the reduced pressure step, the pressurized step comprising bringing the animal-derived decellularized tissue material and the liquid into contact under a pressurized condition,
wherein the reduced pressure step is performed at a vacuum degree of −0.01 to −0.101 MPa.
2. The method according to claim 1, wherein the pressurized step is performed at 0.1 to 1000 atmosphere pressure.
3. The method according to claim 1, wherein the decellularized tissue material is a lyophilized decellularized tissue.
4. The method according to claim 3, wherein the decellularized tissue material is a decellularized tissue lyophilized after being immersed in a treatment solution.
5. The method according to claim 4, wherein the solution comprises a functionality imparting agent.

* * * * *